United States Patent

Habeck et al.

Patent Number: 6,132,703
Date of Patent: Oct. 17, 2000

[54] COSMETIC AND PHARMACEUTICAL PREPARATIONS CONTAINING PHOTOSTABLE UV FILTERS

[75] Inventors: Thorsten Habeck, Meckenheim; Alfred Krause, Speyer, both of Germany

[73] Assignee: BASF Aktiengesellschaft, Ludwigshafen, Germany

[21] Appl. No.: 09/247,543

[22] Filed: Feb. 10, 1999

[30] Foreign Application Priority Data

Feb. 16, 1998 [DE] Germany .................. 198 06 241

[51] Int. Cl.[7] .................. A61K 07/42; A61K 7/44; A61K 7/00
[52] U.S. Cl. .................. 424/59; 424/60; 424/400; 424/401
[58] Field of Search .................. 424/59, 60, 400, 424/401

[56] References Cited

U.S. PATENT DOCUMENTS

| | | |
|---|---|---|
| 3,278,448 | 10/1966 | Lamerer et al. |
| 4,387,089 | 6/1983 | De Polo .................. 424/59 |
| 5,576,354 | 11/1996 | Deflandre et al. .................. 514/685 |
| 5,587,150 | 12/1996 | Deflandre et al. .................. 424/59 |

FOREIGN PATENT DOCUMENTS

| | | |
|---|---|---|
| 100651 | 2/1984 | European Pat. Off. . |
| 251398 | 1/1988 | European Pat. Off. . |
| 514491 | 11/1992 | European Pat. Off. . |
| 852137 | 7/1998 | European Pat. Off. . |
| 7927680 | 6/1980 | France . |
| 1087902 | 6/1956 | Germany . |
| 98/14423 | 4/1998 | WIPO . |

*Primary Examiner*—Shelley A. Dodson
*Attorney, Agent, or Firm*—Keil & Weinkauf

[57] ABSTRACT

Malonic ester derivatives of the formula I

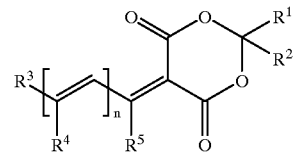

where the variables have the meaning explained in the description, as photostable UV filters in cosmetic and pharmaceutical preparations for protecting the human skin or human hair from the sun's rays, alone or together with compounds absorbing in the UV region and known for cosmetic and pharmaceutical preparations.

2 Claims, No Drawings

COSMETIC AND PHARMACEUTICAL PREPARATIONS CONTAINING PHOTOSTABLE UV FILTERS

The invention relates to the use of malonic ester derivatives as photostable UV filters in cosmetic and pharmaceutical preparations for protecting the human epidermis or human hair from UV radiation, specifically in the range from 320 to 400 nm.

The sunscreens employed in cosmetic and pharmaceutical preparations have the task of preventing, or at least diminishing the consequences of, the harmful effects of sunlight on the human skin. However, these sunscreens also serve to protect other ingredients from decomposition or breakdown by UV radiation. The intention in hair cosmetic formulations is to reduce damage to the keratin fibers by UV rays.

The sunlight reaching the surface of the earth contains UV-B radiation (280 to 320 nm) and UV-A radiation (>320 nm), which are directly adjacent to the invisible light region. The effect on the human skin is manifested, particularly with UV-B radiation, by sunburn. Accordingly, the industry supplies a relatively large number of substances which absorb UV-B radiation and thus prevent sunburn.

Dermatological investigations have now shown that UV-A radiation is also perfectly able to cause skin damage and allergies by, for example, damaging the keratin or elastin. This reduces the elasticity and water storage capacity of the skin, i.e. the skin becomes less supple and tends to form wrinkles. The noticeably high incidence of skin cancer in regions where the sun's radiation is strong shows that damage to the genetic information in the cells is evidently also caused by sunlight, specifically by UV-A radiation. All these findings therefore make it appear necessary to develop efficient filter substances for the UV-A region.

There is a growing demand for sunscreens for cosmetic and pharmaceutical preparations which can be used in particular as UV-A filters and whose absorption maximum ought therefore to be in the range from about 320 to 380 nm. In order to achieve the required effect by using the minimum amount, sunscreens of this type ought additionally to have a high specific extinction. Sunscreens for cosmetic products must also meet a large number of other requirements, for example good solubility in cosmetic oils, high stability of the emulsions produced with them, toxicological acceptability, and low intrinsic odor and little intrinsic color.

Another requirement which sunscreens must meet is adequate photostability. However, this is only inadequately ensured, if at all, with UV-A-absorbing sunscreens available to date.

French Patent No. 2 440 933 describes 4-(1,1-dimethylethyl)-4'-methoxydibenzoylmethane as UV-A filter. It is proposed to combine this specific UV-A filter, which is sold by GIVAUDAN under the name "PARSOL 1789", with various UV-B filters in order to absorb all UV rays with a wavelength from 280 to 380 nm.

However, this UV-A filter does not have sufficient photochemical stability, when it is used alone or in combination with UV-B filters, to ensure sustained protection of the skin during lengthy sunbathing, which means that repeated applications at regular and short intervals are required if effective protection of the skin from all UV rays is desired.

For this reason, EP-A-0 514 491 discloses the stabilization of insufficiently photostable UV-A filters by adding 2-cyano-3,3-diphenylacrylic esters which themselves act as filters in the UV-B region.

It has additionally been proposed in EP-A-0 251 398 to combine chromophores absorbing UV-A radiation and Uv-B radiation into one molecule by using a linker. This has the disadvantage that a free combination of UV-A and UV-B filters in the cosmetic preparation is no longer possible, and that difficulties in the chemical linkage of the chromophores allow only certain combinations.

German Patent No. 1 087 902 describes the use of condensates of hydroxy- and alkoxybenzaldehydes and carbon acids as UV filters in industrial applications, for example in plastics, but not in cosmetic or pharmaceutical preparations.

It is an object of the present invention to propose sunscreens for cosmetic and pharmaceutical purposes which absorb in the UV-A region with high extinction, are photostabile, have little intrinsic color, i.e. a sharp band structure, and are soluble in oil or water depending on the substituent.

We have found that this object is achieved by the use of malonic ester derivatives of the formula I,

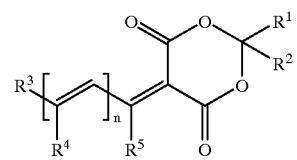

in which the variables have the following meanings, independently of one another:

$R^1$ and $R^2$ hydrogen, $C_1$–$C_{20}$-alkyl,
where $R^1$ and $R^2$ may together form a 5- to 12-membered ring;

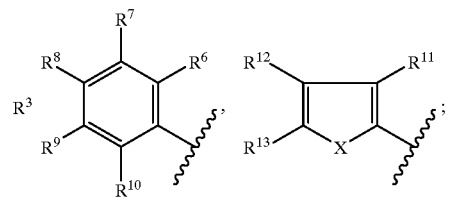

$R^4$ hydrogen, $C_1$–$C_{20}$-alkyl,

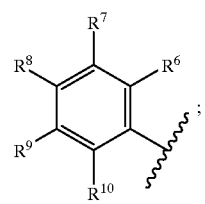

$R^5$ hydrogen, $C_1$–$C_{20}$-alkyl, OH,

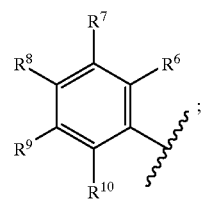

$R^6$ to $R^{13}$ hydrogen, OH, $C_1$–$C_{20}$-alkyl, $C_2$–$C_{10}$-alkenyl, $C_3$–$C_{10}$-cycloalkyl, $C_3$–$C_{10}$-cycloalkenyl, $C_1$–$C_{12}$- alkoxy, $C_1$–$C_{20}$-alkoxycarbonyl, $C_1$–$C_{12}$-alkylamino, $C_1$–$C_{12}$-dialkylamino, aryl, hetaryl, unsubstituted or substituted, substances which confer solubility in water and are selected from the group consisting of carboxylate, sulfonate or ammonium residues;

X O, S, NH;

n 0, 1 as photostable WU-filter in cosmetic and pharmaceutical preparations for protecting the human skin or human hair from the sun's rays, alone or together with compounds which absorb in the UV region and are known per se for cosmetic and pharmaceutical preparations.

Alkyl radicals which may be mentioned for $R^1$ and $R^2$ and for $R^4$ to $R^{13}$ are branched or unbranched $C_1$–$C_{20}$-alkyl chains, preferably ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

The substituents $R^1$ and $R^2$ may also together form a cycloalkyl radical containing 5 to 12 carbon atoms. Those to be mentioned as preferred are cyclopentyl, cyclohexyl, cyclooctyl and cyclododecyl.

Alkenyl radicals which may be mentioned for $R^6$ to $R^{13}$ are branched or unbranched $C_2$–$C_{10}$-alkenyl chains, preferably vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

Cycloalkyl radicals which may be mentioned for $R^6$ to $R^{13}$ are preferably unsubstituted or alkyl-substituted $C_3$–$C_{10}$-cycloalkyl rings such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-2-butylcyclopropyl, 1,2-dimethylcyclopropyl, 1-methyl-2-ethylcyclopropyl, cyclooctyl, cyclononyl or cyclodecyl.

Cycloalkenyl radicals which may be mentioned for $R^6$ to $R^{13}$ are preferably unsubstituted or alkyl-substituted $C_3$–$C_{10}$-cycloalkenyl rings with one or more double bonds such as cyclopropenyl, cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecenyl.

The cycloalkenyl and cycloalkyl radicals may be unsubstituted or substituted by one or more, e.g. 1 to 3, radicals such as halogen, e.g. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals, or contain 1 to 3 heteroatoms such as sulfur, nitrogen, whose free valences can be saturated by hydrogen or $C_1$–$C_4$-alkyl, or oxygen in the ring.

Suitable alkoxy radicals for $R^6$ to $R^{13}$ are those having 1 to 12 carbon atoms, preferably having 1 to 8 carbon atoms.

Examples which may be mentioned are:

| | |
|---|---|
| methoxy- | ethoxy- |
| isopropoxy- | n-propoxy- |
| 1-methylpropoxy- | n-butoxy- |
| n-pentoxy- | 2-methylpropoxy- |
| 3-methylbutoxy- | 1,1-dimethylpropoxy- |
| 2,2-dimethylpropoxy- | hexoxy- |
| 1-methyl-1-ethylpropoxy- | heptoxy- |
| octoxy- | 2-ethylhexoxy- |

Examples of alkoxycarbonyl radicals for $R^6$ to $R^{13}$ are those containing the abovementioned alkoxy radicals or radicals derived from higher alcohols (fatty alcohols) having up to 20 carbon atoms.

Suitable mono- or dialkylamino radicals for $R^6$ to $R^{13}$ are those containing alkyl radicals having 1 to 12 carbon atoms, such as methyl, n-propyl, n-butyl, 2-methylpropyl, 1,1-dimethylpropyl, hexyl, heptyl, 2-ethylhexyl, isopropyl, 1-methylpropyl, n-pentyl, 3-methylbutyl, 2,2-dimethylpropyl, 1-methyl-1-ethylpropyl and octyl.

Aryl means aromatic rings or ring systems having 6 to 18 carbon atoms in the ring system, for example phenyl or naphthyl, each of which may be unsubstituted or substituted by one or more radicals such as halogen, e.g. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals. Unsubstituted or substituted phenyl, methoxyphenyl and naphthyl are preferred.

Hetaryl radicals are advantageously simple or fused aromatic ring systems having one or more heteroaromatic 3- to 7-membered rings. Heteroatoms which may be present in the ring or ring system are one or more nitrogen, sulfur and/or oxygen atoms.

Hydrophilic radicals, i.e. those making it possible for compounds of the formula I to dissolve in water, for $R^1$ and $R^2$ are, for example, carboxyl and sulfo radicals and, in particular, their salts with any physiologically tolerated cations, such as the alkali metal salts or such as the trialkylammonium salts, such as tri(hydroxyalkyl)ammonium salts or the 2-hydroxymethyl-2-propyl-ammonium salts. Also suitable are armonium radicals, especially alkylammonium radicals, with any physiologically tolerated anions.

Preferred compounds of the formula I are those in which $R^1$ and $R^2$ are $C_1$–$C_{12}$-alkyl, where $R^1$ and $R^2$ may together form a 5- to 12-membered ring;

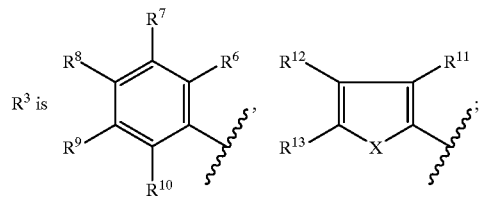

$R^5$ is hydrogen;
$R^6$ to $R^{13}$ are hydrogen, OH, $C_1$-$C_{12}$-alkyl, $C_1$-$C_8$-alkoxy, $C_1$-$C_{12}$-alkoxycarbonyl,
substituents which confer solubility in water and are selected from the group consisting of carboxylates, sulfonate or ammonium residues;

-continued

| | |
|---|---|
| X | is O, S, NH; |
| n | is 0. |

Alkyl radicals which may be mentioned as preferred for $R^1$ and $R^2$ and for $R^6$ to $R^{13}$ are branched or unbranched $C_1$–$C_{12}$-alkyl chains, particularly preferably ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl.

The substituents $R^1$ and $R^2$ may also together form a cycloalkyl radicla containing 5 to 12 carbon atoms. Cyclopentyl, cyclohexyl and cyclooctyl should be mentioned as preferred.

Suitable alkoxy radicals for $R^6$ to $R^{13}$ are those having 1 to 8 carbon atoms, preferably having 1 to 4 carbon atoms. Examples which may be mentioned are:

| | |
|---|---|
| methoxy- | ethoxy- |
| isopropoxy- | n-propoxy- |
| 1-methylpropoxy- | 2-methylpropoxy- |
| n-butoxy- | |

Examples of preferred alkoxycarbonyl radicals for $R^6$ to $R^{13}$ are those containing the abovementioned alkoxy radicals or radicals derived from higher alcohols having up to 12 carbon atoms.

Particularly preferred radicals for $R^3$ are, inter alia, phenyl, para-substituted phenyl and ortho-disubstituted phenyl and meta, para, meta-trisubstituted phenyl, where the substituents $R^6$ to $R^{10}$ may have the abovementioned meanings.

In addition, compounds of the formula I having special photostable properties are those in which the substituents $R^1$ and $R^2$ and $R^6$ to $R^{10}$ are in the combination mentioned in Tables 1a and 1b:

TABLE 1a

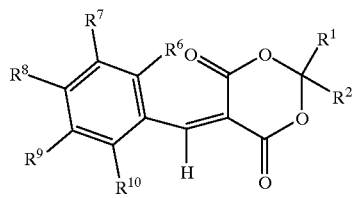

| $R^1$ | $R^2$ | $R^6$ | $R^7$ | $R^8$ | $R^9$ | $R^{10}$ |
|---|---|---|---|---|---|---|
| Methyl | Methyl | H | H | H | H | H |
| Ethyl | Ethyl | H | H | H | H | H |
| n-Propyl | n-Propyl | H | H | H | H | H |
| i-Propyl | i-Propyl | H | H | H | H | H |
| n-Butyl | n-Butyl | H | H | H | H | H |
| i-Butyl | i-Butyl | H | H | H | H | H |
| n-Pentyl | n-Pentyl | H | H | H | H | H |
| n-Hexyl | n-Hexyl | H | H | H | H | H |
| n-Octyl | n-Octyl | H | H | H | H | H |
| Methyl | Methyl | H | H | Methoxy | H | H |
| Ethyl | Ethyl | H | H | Methoxy | H | H |
| n-Propyl | n-Propyl | H | H | Methoxy | H | H |
| i-Propyl | i-Propyl | H | H | Methoxy | H | H |
| n-Butyl | n-Butyl | H | H | Methoxy | H | H |
| i-Butyl | i-Butyl | H | H | Methoxy | H | H |
| n-Pentyl | n-Pentyl | H | H | Methoxy | H | H |
| n-Hexyl | n-Hexyl | H | H | Methoxy | H | H |
| n-Octyl | n-Octyl | H | H | Methoxy | H | H |
| Methyl | Methyl | H | H | Ethoxy | H | H |
| Ethyl | Ethyl | H | H | Ethoxy | H | H |
| n-Propyl | n-Propyl | H | H | Ethoxy | H | H |
| i-Propyl | i-Propyl | H | H | Ethoxy | H | H |
| n-Butyl | n-Butyl | H | H | Ethoxy | H | H |
| i-Butyl | i-Butyl | H | H | Ethoxy | H | H |
| n-Pentyl | n-Pentyl | H | H | Ethoxy | H | H |
| n-Hexyl | n-Hexyl | H | H | Ethoxy | H | H |
| n-Octyl | n-Octyl | H | H | Ethoxy | H | H |
| Methyl | Methyl | H | H | n-Propoxy | H | H |
| Ethyl | Ethyl | H | H | n-Propoxy | H | H |
| n-Propyl | n-Propyl | H | H | n-Propoxy | H | H |
| i-Propyl | i-Propyl | H | H | n-Propoxy | H | H |
| n-Butyl | n-Butyl | H | H | n-Propoxy | H | H |
| i-Butyl | i-Butyl | H | H | n-Propoxy | H | H |
| n-Pentyl | n-Pentyl | H | H | n-Propoxy | H | H |
| n-Hexyl | n-Hexyl | H | H | n-Propoxy | H | H |
| n-Octyl | n-Octyl | H | H | n-Propoxy | H | H |
| Methyl | Methyl | H | H | i-Propoxy | H | H |

TABLE 1a-continued

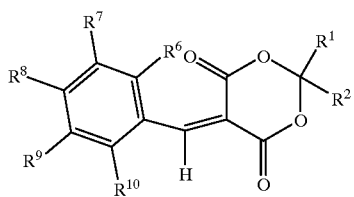

| R¹ | R² | R⁶ | R⁷ | R⁸ | R⁹ | R¹⁰ |
| --- | --- | --- | --- | --- | --- | --- |
| Ethyl | Ethyl | H | H | i-Propoxy | H | H |
| n-Propyl | n-Propyl | H | H | i-Propoxy | H | H |
| i-Propyl | i-Propyl | H | H | i-Propoxy | H | H |
| n-Butyl | n-Butyl | H | H | i-Propoxy | H | H |
| i-Butyl | i-Butyl | H | H | i-Propoxy | H | H |
| n-Pentyl | n-Pentyl | H | H | i-Propoxy | H | H |
| n-Hexyl | n-Hexyl | H | H | i-Propoxy | H | H |
| n-Octyl | n-Octyl | H | H | i-Propoxy | H | H |
| Methyl | Methyl | H | H | n-Butoxy | H | H |
| Ethyl | Ethyl | H | H | n-Butoxy | H | H |
| n-Propyl | n-Propyl | H | H | n-Butoxy | H | H |
| i-Propyl | i-Propyl | H | H | n-Butoxy | H | H |
| n-Butyl | n-Butyl | H | H | n-Butoxy | H | H |
| i-Butyl | i-Butyl | H | H | n-Butoxy | H | H |
| n-Pentyl | n-Pentyl | H | H | n-Butoxy | H | H |
| n-Hexyl | n-Hexyl | H | H | n-Butoxy | H | H |
| n-Octyl | n-Octyl | H | H | n-Butoxy | H | H |
| Methyl | Methyl | H | Methyl | OH | Methyl | H |
| Ethyl | Ethyl | H | Methyl | OH | Methyl | H |
| n-Propyl | n-Propyl | H | Methyl | OH | Methyl | H |
| i-Propyl | i-Propyl | H | Methyl | OH | Methyl | H |
| n-Butyl | n-Butyl | H | Methyl | OH | Methyl | H |
| i-Butyl | i-Butyl | H | Methyl | OH | Methyl | H |
| n-Pentyl | n-Pentyl | H | Methyl | OH | Methyl | H |
| n-Hexyl | n-Hexyl | H | Methyl | OH | Methyl | H |
| n-Octyl | n-Octyl | H | Methyl | OH | Methyl | H |
| Methyl | Methyl | H | Ethyl | OH | Ethyl | H |
| Ethyl | Ethyl | H | Ethyl | OH | Ethyl | H |
| n-Propyl | n-Propyl | H | Ethyl | OH | Ethyl | H |
| i-Propyl | i-Propyl | H | Ethyl | OH | Ethyl | H |
| n-Butyl | n-Butyl | H | Ethyl | OH | Ethyl | H |
| i-Butyl | i-Butyl | H | Ethyl | OH | Ethyl | H |
| n-Pentyl | n-Pentyl | H | Ethyl | OH | Ethyl | H |
| n-Hexyl | n-Hexyl | H | Ethyl | OH | Ethyl | H |
| n-Octyl | n-Octyl | H | Ethyl | OH | Ethyl | H |
| Methyl | Methyl | H | i-Propyl | OH | i-Propyl | H |
| Ethyl | Ethyl | H | i-Propyl | OH | i-Propyl | H |
| n-Propyl | n-Propyl | H | i-Propyl | OH | i-Propyl | H |
| i-Propyl | i-Propyl | H | i-Propyl | OH | i-Propyl | H |
| n-Butyl | n-Butyl | H | i-Propyl | OH | i-Propyl | H |
| i-Butyl | i-Butyl | H | i-Propyl | OH | i-Propyl | H |
| n-Pentyl | n-Pentyl | H | i-Propyl | OH | i-Propyl | H |
| n-Hexyl | n-Hexyl | H | i-Propyl | OH | i-Propyl | H |
| n-Octyl | n-Octyl | H | i-Propyl | OH | i-Propyl | H |
| Methyl | Methyl | H | n-Butyl | OH | n-Butyl | H |
| Ethyl | Ethyl | H | n-Butyl | OH | n-Butyl | H |
| n-Propyl | n-Propyl | H | n-Butyl | OH | n-Butyl | H |
| i-Propyl | i-Propyl | H | n-Butyl | OH | n-Butyl | H |
| n-Butyl | n-Butyl | H | n-Butyl | OH | n-Butyl | H |
| i-Butyl | i-Butyl | H | n-Butyl | OH | n-Butyl | H |
| n-Pentyl | n-Pentyl | H | n-Butyl | OH | n-Butyl | H |
| n-Hexyl | n-Hexyl | H | n-Butyl | OH | n-Butyl | H |
| n-Octyl | n-Octyl | H | n-Butyl | OH | n-Butyl | H |
| Methyl | Methyl | H | t-Butyl | OH | t-Butyl | H |
| Ethyl | Ethyl | H | t-Butyl | OH | t-Butyl | H |
| n-Propyl | n-Propyl | H | t-Butyl | OH | t-Butyl | H |
| i-Propyl | i-Propyl | H | t-Butyl | OH | t-Butyl | H |
| n-Butyl | n-Butyl | H | t-Butyl | OH | t-Butyl | H |
| i-Butyl | i-Butyl | H | t-Butyl | OH | t-Butyl | H |
| n-Pentyl | n-Pentyl | H | t-Butyl | OH | t-Butyl | H |
| n-Hexyl | n-Hexyl | H | t-Butyl | OH | t-Butyl | H |
| n-Octyl | n-Octyl | H | t-Butyl | OH | t-Butyl | H |
| Methyl | Methyl | | H | | H | H |
| Ethyl | Ethyl | | H | | H | H |
| n-Propyl | n-Propyl | | H | | H | H |
| i-Propyl | i-Propyl | | H | | H | H |

TABLE 1a-continued $$\text{structure with } R^1, R^2, R^6, R^7, R^8, R^9, R^{10}$$

| R¹ | R² | R⁶ | R⁷ | R⁸ | R⁹ | R¹⁰ |
|---|---|---|---|---|---|---|
| n-Butyl | n-Butyl | | H | | H | H |
| i-Butyl | i-Butyl | | H | | H | H |
| n-Pentyl | n-Pentyl | | H | | H | H |
| n-Hexyl | n-Hexyl | | H | | H | H |
| n-Octyl | n-Octyl | | H | | H | H |
| Methyl | Methyl | Ethyl | H | Ethyl | H | H |
| Ethyl | Ethyl | Ethyl | H | Ethyl | H | H |
| n-Propyl | n-Propyl | Ethyl | H | Ethyl | H | H |
| i-Propyl | i-Propyl | Ethyl | H | Ethyl | H | H |
| n-Butyl | n-Butyl | Ethyl | H | Ethyl | H | H |
| i-Butyl | i-Butyl | Ethyl | H | Ethyl | H | H |
| n-Pentyl | n-Pentyl | Ethyl | H | Ethyl | H | H |
| n-Hexyl | n-Hexyl | Ethyl | H | Ethyl | H | H |
| n-Octyl | n-Octyl | Ethyl | H | Ethyl | H | H |
| Methyl | Methyl | n-Propyl | H | n-Propyl | H | H |
| Ethyl | Ethyl | n-Propyl | H | n-Propyl | H | H |
| n-Propyl | n-Propyl | n-Propyl | H | n-Propyl | H | H |
| i-Propyl | i-Propyl | n-Propyl | H | n-Propyl | H | H |
| n-Butyl | n-Butyl | n-Propyl | H | n-Propyl | H | H |
| i-Butyl | i-Butyl | n-Propyl | H | n-Propyl | H | H |
| n-Pentyl | n-Pentyl | n-Propyl | H | n-Propyl | H | H |
| n-Hexyl | n-Hexyl | n-Propyl | H | n-Propyl | H | H |
| n-Octyl | n-Octyl | n-Propyl | H | n-Propyl | H | H |
| Methyl | Methyl | i-Propyl | H | i-Propyl | H | H |
| Ethyl | Ethyl | i-Propyl | H | i-Propyl | H | H |
| n-Propyl | n-Propyl | i-Propyl | H | i-Propyl | H | H |
| i-Propyl | i-Propyl | i-Propyl | H | i-Propyl | H | H |
| n-Butyl | n-Butyl | i-Propyl | H | i-Propyl | H | H |
| i-Butyl | i-Butyl | i-Propyl | H | i-Propyl | H | H |
| n-Pentyl | n-Pentyl | i-Propyl | H | i-Propyl | H | H |
| n-Hexyl | n-Hexyl | i-Propyl | H | i-Propyl | H | H |
| n-Octyl | n-Octyl | i-Propyl | H | i-Propyl | H | H |
| Methyl | Methyl | n-Butyl | H | n-Butyl | H | H |
| Ethyl | Ethyl | n-Butyl | H | n-Butyl | H | H |
| n-Propyl | n-Propyl | n-Butyl | H | n-Butyl | H | H |
| i-Propyl | i-Propyl | n-Butyl | H | n-Butyl | H | H |
| n-Butyl | n-Butyl | n-Butyl | H | n-Butyl | H | H |
| i-Butyl | i-Butyl | n-Butyl | H | n-Butyl | H | H |
| n-Pentyl | n-Pentyl | n-Butyl | H | n-Butyl | H | H |
| n-Hexyl | n-Hexyl | n-Butyl | H | n-Butyl | H | H |
| n-Octyl | n-Octyl | n-Butyl | H | n-Butyl | H | H |
| Methyl | Methyl | t-Butyl | H | t-Butyl | H | H |
| Ethyl | Ethyl | t-Butyl | H | t-Butyl | H | H |
| n-Propyl | n-Propyl | t-Butyl | H | t-Butyl | H | H |
| i-Propyl | i-Propyl | t-Butyl | H | t-Butyl | H | H |
| n-Butyl | n-Butyl | t-Butyl | H | t-Butyl | H | H |
| i-Butyl | i-Butyl | t-Butyl | H | t-Butyl | H | H |
| n-Pentyl | n-Pentyl | t-Butyl | H | t-Butyl | H | H |
| n-Hexyl | n-Hexyl | t-Butyl | H | t-Butyl | H | H |
| n-Octyl | n-Octyl | t-Butyl | H | t-Butyl | H | H |

TABLE 1b

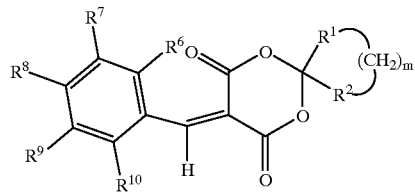

| R¹ | R² | m | R⁶ | R⁷ | R⁸ | R⁹ | R¹⁰ |
|---|---|---|---|---|---|---|---|
| Methylene | Methylene | 2 | H | H | H | H | H |
| Methylene | Methylene | 3 | H | H | H | H | H |
| Methylene | Methylene | 5 | H | H | H | H | H |
| Methylene | Methylene | 2 | H | H | Methoxy | H | H |
| Methylene | Methylene | 3 | H | H | Methoxy | H | H |
| Methylene | Methylene | 5 | H | H | Methoxy | H | H |
| Methylene | Methylene | 2 | H | H | Ethoxy | H | H |
| Methylene | Methylene | 3 | H | H | Ethoxy | H | H |
| Methylene | Methylene | 5 | H | H | Ethoxy | H | H |
| Methylene | Methylene | 2 | H | H | n-Propoxy | H | H |
| Methylene | Methylene | 3 | H | H | n-Propoxy | H | H |
| Methylene | Methylene | 5 | H | H | n-Propoxy | H | H |
| Methylene | Methylene | 2 | H | H | i-Propoxy | H | H |
| Methylene | Methylene | 3 | H | H | i-Propoxy | H | H |
| Methylene | Methylene | 5 | H | H | i-Propoxy | H | H |
| Methylene | Methylene | 2 | H | H | n-Butoxy | H | H |
| Methylene | Methylene | 3 | H | H | n-Butoxy | H | H |
| Methylene | Methylene | 5 | H | H | n-Butoxy | H | H |
| Methylene | Methylene | 2 | H | Methyl | OH | Methyl | H |
| Methylene | Methylene | 3 | H | Methyl | OH | Methyl | H |
| Methylene | Methylene | 5 | H | Methyl | OH | Methyl | H |
| Methylene | Methylene | 2 | H | Ethyl | OH | Ethyl | H |
| Methylene | Methylene | 3 | H | Ethyl | OH | Ethyl | H |
| Methylene | Methylene | 5 | H | Ethyl | OH | Ethyl | H |
| Methylene | Methylene | 2 | H | i-Propyl | OH | i-Propyl | H |
| Methylene | Methylene | 3 | H | i-Propyl | OH | i-Propyl | H |
| Methylene | Methylene | 5 | H | i-Propyl | OH | i-Propyl | H |
| Methylene | Methylene | 2 | H | n-Butyl | OH | n-Butyl | H |
| Methylene | Methylene | 3 | H | n-Butyl | OH | n-Butyl | H |
| Methylene | Methylene | 5 | H | n-Butyl | OH | n-Butyl | H |
| Methylene | Methylene | 2 | H | t-Butyl | OH | t-Butyl | H |
| Methylene | Methylene | 3 | H | t-Butyl | OH | t-Butyl | H |
| Methylene | Methylene | 5 | H | t-Butyl | OH | t-Butyl | H |
| Methylene | Methylene | 2 |  | H |  | H | H |
| Methylene | Methylene | 3 |  | H |  | H | H |
| Methylene | Methylene | 5 |  | H |  | H | H |
| Methylene | Methylene | 2 | Ethyl | H | Ethyl | H | H |
| Methylene | Methylene | 3 | Ethyl | H | Ethyl | H | H |
| Methylene | Methylene | 5 | Ethyl | H | Ethyl | H | H |
| Methylene | Methylene | 2 | n-Propyl | H | n-Propyl | H | H |
| Methylene | Methylene | 3 | n-Propyl | H | n-Propyl | H | H |
| Methylene | Methylene | 5 | n-Propyl | H | n-Propyl | H | H |
| Methylene | Methylene | 2 | i-Propyl | H | i-Propyl | H | H |
| Methylene | Methylene | 3 | i-Propyl | H | i-Propyl | H | H |
| Methylene | Methylene | 5 | i-Propyl | H | i-Propyl | H | H |
| Methylene | Methylene | 2 | n-Butyl | H | n-Butyl | H | H |
| Methylene | Methylene | 3 | n-Butyl | H | n-Butyl | H | H |
| Methylene | Methylene | 5 | n-Butyl | H | n-Butyl | H | H |
| Methylene | Methylene | 2 | t-Butyl | H | t-Butyl | H | H |
| Methylene | Methylene | 3 | t-Butyl | H | t-Butyl | H | H |
| Methylene | Methylene | 5 | t-Butyl | H | t-Butyl | H | H |

The present invention also relates to the cosmetic and pharmaceutical preparations which comprise from 0.1 to 10% by weight, preferably 1 to 7% by weight, based on the total amount of the cosmetic and pharmaceutical preparation, of one or more of the compounds of the formula I together with compounds known per se for cosmetic and pharmaceutical preparations and absorbing in the UV-B region as sunscreens, generally employing the compounds of the formula I in a smaller amount than the UV-B-absorbing compounds.

Most of the sunscreens in the cosmetic and pharmaceutical preparations used to protect the human epidermis consist of compounds which absorb UV light in the UV-B region, i.e. in the region from 280 to 320 nm. The content of UV-A absorbers to be used according to the invention is, for example, from 10 to 90% by weight, preferably 20 to 50% by weight, based on the total amount of UV-B and UV-A absorbing substances.

The sunscreen-containing cosmetic and pharmaceutical preparations are, as a rule, based on a carrier which contains at least one oil phase. However, preparations with an exclusively aqueous basis are also possible on use of compounds with hydrophilic substituents. Accordingly, oils, oil-in-water and water-in-oil emulsions, creams and pastes, protective lipstick bases or non-greasy gels are suitable.

Sunscreen products of these types can accordingly be in liquid, pasty or solid form, for example as water-in-oil creams, oil-in-water creams and lotions, aerosol foam creams, gels, oils, grease sticks, dusting powders, sprays or hydroalcoholic lotions.

Examples of conventional cosmetic oil components are liquid paraffin, glyceryl stearate, isopropyl myristate, diisopropyl adipate, cetylstearyl 2-ethylhexanoate, hydrogenated polyisobutene, petrolatum, caprylic/capric acids triglycerides, microcrystalline wax, lanolin and stearic acid.

Conventional cosmetic ancillary substances which may be suitable as additives are, for example, coemulsifiers, fats and waxes, stabilizers, thickeners, biogenic active substances, film formers, fragrances, dyes, pearlescent agents, preservatives, pigments, electrolytes (e.g. magnesium sulfate) and pH regulators. Suitable and preferred coemulsifiers are known W/O and O/W emulsifiers such as polyglycerol esters, sorbitan esters or partially esterified glycerides. Typical examples of fats are glycerides; waxes which may be mentioned are, inter alia, beeswax, paraffin wax or microwaxes, possibly combined with hydrophilic waxes. Stabilizers which can be employed are metal salts of fatty acids such as magnesium, aluminum and/or zinc stearate. Examples of suitable thickeners are crosslinked polyacrylic acids and their derivatives, polysaccharides, in particular xanthan gum, guar-guar, agar-agar, alginates and Tyloses, carboxymethylcellulose and hydroxyethylcellulose, also fatty alcohols, monoglycerides and fatty acids, polyacrylates, polyvinyl alcohol and polyvinylpyrrolidone. Examples of biogenic active substances are plant extracts, protein hydrolysates and vitamin complexes. Examples of film formers which are in use are hydrocolloids such as chitosan, microcrystalline chitosan or quaternized chitosan, polyvinylpyrrolidone, vinylpyrrolidone/vinyl acetate copolymers, polymers of the acrylic acid series, quaternary cellulose derivates and similar compounds. Examples of suitable preservatives are formaldehyde solution, p-hydroxybenzoate or sorbic acid. Examples of suitable pearlscent agents are glycol distearic esters such as ethylene glycol distearate, but also fatty acids and fatty acid monoglycol ester. Dyes which can be used are the substances suitable and approved for cosmetic purposes, as tabulated, for example, in the publication "Kosmetische Färbemittel" of the Farbstoffkommission der Deutschen Forschungsgemeinschaft, published by Verlag Chemie, Weinheim, 1984. These dyes are normally employed in a concentration of from 0.001 to 0.1% of the total weight of the mixture.

The total content of ancillary substances and additives can be from 1 to 80, preferably 6 to 40, % by weight, and the nonaqueous content ("active substance") can be from 20 to 80, preferably 30 to 70, % by weight, based on the composition. The compositions can be produced in a manner known per se, i.e. for example by hot, cold, hot/cold or PIT emulsification. This is a purely mechanical process; no chemical reaction takes place.

Finally, it is also possible to use other substances which absorb in the UV-A region and are known per se as long as they are stable in the complete system of the combination of UV-B and UV-A filters to be used according to the invention.

Any UV-A and UV-B filter substances are suitable as UV filter subtances which are used in combiantion with the compounds of the formula I to be used according to the invention, including those mentioned in Table 2.

TABLE 2

| No. | Substance | CAS No. (= acid) |
|---|---|---|
| 1 | 4-Aminobenzoic acid | 150-13-0 |
| 2 | 3-(4-Trimethylammonium)benzylidenebornan-2-one methyl sulfate | 52793-97-2 |
| 3 | 3,3,5-Trimethylcyclohexyl salicylate (homosalate) | 118-56-9 |
| 4 | 2-Hydroxy-4-methoxybenzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylendimethine)bis(7,7-dimethyl-2-oxobicyclo[2.2.1]heptane-1-methanesulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfonic acid (sulisobenzone) and the sodium salt | 4065-45-6 |
| 13 | 3-(4-Methylbenzylidene)bornan-2-one | 36861-47-9 |
| 14 | 3-Benzylidenebornan-2-one | 15087-24-8 |
| 15 | 1-(4-Isopropylphenyl)-3-phenylpropane-1,3-dione | 63250-25-9 |
| 16 | 4-Isopropylbenzyl salicylate | 94134-93-7 |
| 17 | 2,4,6-Trio(o-2-ethylhexyoxycarbonylanilino)-1,3,5-triazine | 88122-99-0 |
| 18 | 3-(4-Imidazolyl)acrylic acid and its ethyl ester | 104-98-3 |
| 19 | Ethyl 2-cyano-3,3-diphenylacrylate | 5232-99-5 |
| 20 | 2-Ethylhexyl 2-cyano-3,3-diphenylacrylate | 6197-30-4 |
| 21 | Menthyl o-aminobenzoate or: 5-methyl-2-(1-methylethyl)cyclohexyl 2-aminobenzoate | 134-09-8 |
| 22 | Glyceryl p-aminobenzoate or: 4-aminobenzoic acid 1-glyceryl ester | 136-44-7 |
| 23 | 2,2'-Dihydroxy-4-methoxybenzophenone (dioxybenzone) | 131-53-3 |
| 24 | 2-Hydroxy-4-methoxy-4-methylbenzophenone (mexenone) | 1641-17-4 |
| 25 | Triethanolamine salicylate | 2174-16-5 |
| 26 | Dimethoxyphenylglyoxylic acid or: sodium 3,4-dimethoxyphenylglyoxylate | 4732-70-1 |
| 27 | 3-(4-Sulfobenzylidene)bornan-2-one and its salts | 56039-58-8 |
| 28 | 4-tert-Butyl-4'-methoxydibenzoylmethane | 70356-09-1 |
| 29 | 2,2',4,4'-Tetrahydroxybenzophenone | 131-55-5 |

Finally, mention may also be made of micronized pigments such as titanium dioxide and zinc oxide.

To protect human hair from UV rays, the sunscreens of the formula I according to the invention can be incorporated into shampoos, lotions, gels, hair sprays, aerosol foam creams or emulsions in concentrations of from 0.1 to 10% by weight, preferably 1 to 7% by weight. The particular formulations can be used inter alia for washing, coloring and setting the hair.

The compounds to be used according to the invention as a rule have a particularly high absorbance in the region of UV-A radiation with a sharp band structure. They are furthermore readily soluble in cosmetic oils and can easily be incorporated into cosmetic formulations. Emulsions prepared using the compounds I show particularly high stability, the compounds I themselves show high photostability, and the preparations produced with I have a pleasant skin feel.

The UV filter action of the compounds of the formula I according to the invention can also be utilized for stabilizing active and ancillary substances in cosmetic and pharmaceutical formulations.

The compounds of the formula I claimed for use as sunscreens in cosmetic and pharmaceutical preparations are obtained by condensing an aromatic carbonyl compound of the formula II with cyclic malonic esters of the formula III, where the radicals $R^1$ to $R^5$ are intended to have the meanings stated at the outset:

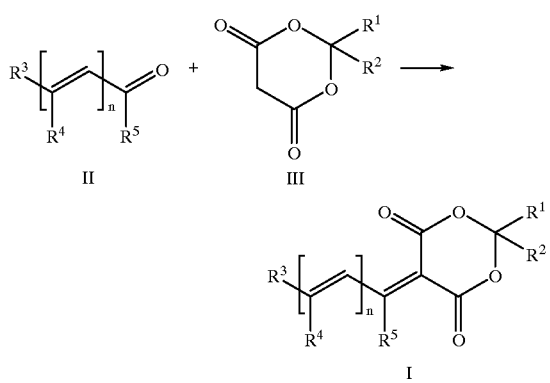

The following examples are intended to illustrate the present invention without restricting it.

EXAMPLE 1

Preparation of compound 1 in Table 3a 0.1 mol of benzaldehyde and 0.1 mol Meldrum's acid were dissolved in 100 ml of methanol, 1 ml of each of piperidine and glacial acetic acid were added and the mixture was refluxed for 5 h. It was then diluted with water and extracted with dichloromethane. The organic phase was stirred with active carbon. The organic phase was filtered off and then dried over sodium sulfate and concentrated in vacuo. 19 g (81% of theory) of the compound 1 in Table 3a were obtained as pale yellow crystals. Purity >99% (GC).

The other compounds 2 to 12 in Tables 3a and 3b were obtained from the appropriately substituted aromatic aldehydes and the relevant malonic esters in analogy to Example 1.

TABLE 3a

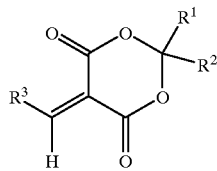

| Number | $R^1$ | $R^2$ | $R^3$ | $\lambda_{max}$ [nm] | $E^1_1$ |
|---|---|---|---|---|---|
| 1 | $CH_3$ | $CH_3$ | Phenyl | 363 | 1200 |
| 2 | $CH_3$ | $CH_3$ | 4-n-Butoxyphenyl | 368 | 960 |
| 3 | $CH_3$ | $C_{11}H_{23}$ | 2-Thienyl | 362 | 615 |
| 4 | $CH_3$ | $CH_3$ | 2-Methylphenyl | 328 | 240 |
| 5 | $CH_3$ | $CH_3$ | 2,4-Dimethylphenyl | 349 | 220 |
| 6 | $CH_3$ | $CH_3$ | 4-Methoxyphenyl | 364 | 1053 |
| 7 | $CH_3$ | $CH_3$ | 3,5-Di-t-butyl-4-OH-phenyl | 374 | 390 |
| 8 | $CH_3$ | $CH_3$ | Benzylidene | 365 | 1380 |
| 9 | $CH_3$ | $C_{11}H_{23}$ | 4-Methoxyphenyl | 364 | 660 |
| 10 | $CH_3$ | $C_{11}H_{23}$ | 3,5-Di-t-butyl-4-OH-phenyl | 384 | 400 |

TABLE 3b

| Number | $R^1$ | $R^2$ | m | $R^3$ | $\lambda_{max}$ [nm] | $E^1_1$ |
|---|---|---|---|---|---|---|
| 11 | $CH_2$ | $CH_2$ | 3 | 4-OH-3-Methoxyphenyl | 376 | 790 |
| 12 | $CH_2$ | $CH_2$ | 3 | 4-Methoxyphenyl | 366 | 940 |

EXAMPLE 2

Standardized method for photostability determination (Suntest)

A 5% by weight alcoholic solution of the sunscreen to be tested is applied, using an Eppendorf pipette (20 μl), to the milled area on a glass plate. Owing to the presence of the alcohol, the solution is distributed uniformly on the roughened glass surface. The amount applied corresponds to the amount of sunscreen required to obtain an average sun protection factor in sun creams. In the test, 4 glass plates are irradiated each time. The evaporation time and the irradiation each last for 30 minutes. The glass plates are cooled slightly during the irradiation by a water cooling system located at the base of the Suntest apparatus. The temperature inside the Suntest apparatus during the irradiation is 40° C. After the samples have been irradiated, they are washed with ethanol into a dark 50 ml graduated flask and measured in a photometer. The blank samples are applied in the same way to glass plates and evaporated at room temperature for 30 minutes. Like the other samples, they are washed off with ethanol and diluted to 100 ml and measured.

The compounds of the formula I according to the invention investigated by the above method showed a photostability of >90%.

General method for preparing emulsions for cosmetic purposes.

All the oil-soluble ingredients are heated to 85° C. in a stirred vessel. When all the ingredients have melted or are present as liquid phase, the aqueous phase is incorporated by homogenization. The emulsion is cooled to about 40° C. with stirring, is perfumed and homogenized, and is then cooled to 25° C. while stirring continuously.

Preparations

EXAMPLE 3

Lip care composition

Mass content % by weight

| | |
|---|---|
| ad 100 | Eucerinum anhydricum |
| 10.00 | glycerol |
| 10.00 | titanium dioxide |
| 5.00 | compound No. 1 in Table 3a |
| 8.00 | octyl methoxycinnamate |
| 5.00 | zinc oxide |
| 4.00 | castor oil |
| 4.00 | pentaerythrityl stearate/caprate/caprylate/adipate |
| 3.00 | glyceryl stearate SE |
| 2.00 | beeswax |

-continued

| | |
|---|---|
| 2.00 | microcrystalline wax |
| 2.00 | quaternium-18 bentonite |
| 1.50 | PEG-45/dodecyl glycol copolymer |

EXAMPLE 4
Sunblocker composition with micropigments
Mass content % by weight

| | |
|---|---|
| ad 100 | water |
| 10.00 | octyl methoxycinnamate |
| 6.00 | PEG-7-hydrogenated castor oil |
| 6.00 | titanium dioxide |
| 5.00 | compound No. 1 in Table 3a |
| 5.00 | mineral oil |
| 5.00 | isoamyl p-methoxycinnamate |
| 5.00 | propylene glycol |
| 3.00 | jojoba oil |
| 3.00 | 4-methylbenzylidenecamphor |
| 2.00 | PEG-45/dodecyl glycol copolymer |
| 1.00 | dimethicone |
| 0.50 | PEG-40-hydrogenated castor oil |
| 0.50 | tocopheryl acetate |
| 0.50 | phenoxyethanol |
| 0.20 | EDTA |

EXAMPLE 5
Non-greasy gel
Mass content % by weight

| | |
|---|---|
| ad 100 | water |
| 8.00 | octyl methoxycinnamate |
| 7.00 | titanium dioxide |
| 5.00 | compound No. 1 in Table 3a |
| 5.00 | Glycerol |
| 5.00 | PEG-25 PABA |
| 1.00 | 4-Methylbenzylidenecamphor |
| 0.40 | Acrylate C10–C30 alkyl acrylate crosspolymer |
| 0.30 | imidazolidinylurea |
| 0.25 | hydroxyethylcellulose |
| 0.25 | sodium methylparaben |
| 0.20 | disodium EDTA |
| 0.15 | fragrance |
| 0.15 | sodium propylparaben |
| 0.10 | sodium hydroxide |

EXAMPLE 6
Sun cream (SPF 20)
Mass content % by weight

| | |
|---|---|
| ad 100 | water |
| 8.00 | octyl methoxycinnamate |
| 8.00 | titanium dioxide |
| 6.00 | PEG-7-hydrogenated castor oil |
| 5.00 | compound No. 1 in Table 3a |
| 6.00 | mineral oil |
| 5.00 | zinc oxide |
| 5.00 | isopropyl palmitate |
| 5.00 | imidazolidinylurea |
| 3.00 | jojoba oil |
| 2.00 | PEG-45/dodecyl glycol copolymer |
| 1.00 | 4-methylbenzylidenecamphor |
| 0.60 | magnesium stearate |
| 0.50 | tocopheryl acetate |

-continued

| | |
|---|---|
| 0.25 | methylparaben |
| 0.20 | disodium EDTA |
| 0.15 | propylparaben |

EXAMPLE 7
Water-resistant suncream
Mass content % by weight

| | |
|---|---|
| ad 100 | water |
| 8.00 | octyl methoxycinnamate |
| 5.00 | PEG-7-hydrogenated castor oil |
| 5.00 | propylene glycol |
| 4.00 | isopropyl palmitate |
| 4.00 | caprylic/capric triglyceride |
| 5.00 | compound No. 1 in Table 3a |
| 4.00 | Glycerol |
| 3.00 | jojoba oil |
| 2.00 | 4-methylbenzylidenecamphor |
| 2.00 | titanium dioxide |
| 1.50 | PEG-45/dodecyl glycol copolymer |
| 1.50 | dimethicone |
| 0.70 | Magnesium sulfate |
| 0.50 | Magnesium stearate |
| 0.15 | fragrance |

EXAMPLE 8
Sun milk (SPF 6)
Mass content % by weight

| | |
|---|---|
| ad 100 | water |
| 10.00 | mineral oil |
| 6.00 | PEG-7-hydrogenated castor oil |
| 5.00 | isopropyl palmitate |
| 3.50 | octyl methoxycinnamate |
| 5.00 | compound No. 1 in Table 3a |
| 3.00 | caprylic/capric triglyceride |
| 3.00 | jojoba oil |
| 2.00 | PEG-45/dodecyl glycol copolymer |
| 0.70 | magnesium sulfate |
| 0.60 | magnesium stearate |
| 0.50 | tocopheryl acetate |
| 0.30 | glycerol |
| 0.25 | methylparaben |
| 0.15 | propylparaben |
| 0.05 | tocopherol |

We claim:

1. A sunscreen-containing cosmetic or pharmaceutical preparation for protecting the human epidermis or human hair from UV light in the region from 280 to 400 nm, which comprises: a cosmetic or pharmaceutical carrier and an effective amount of a photostable UV filter selected from a compound of the formula I

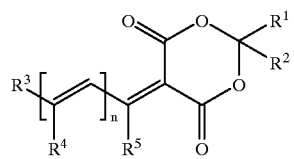

where $R^1$ and $R^2$ independent of each other are hydrogen or $C_1$–$C_{20}$-alkyl, where $R^1$ and $R^2$ may together form a 5- to 12-membered ring;

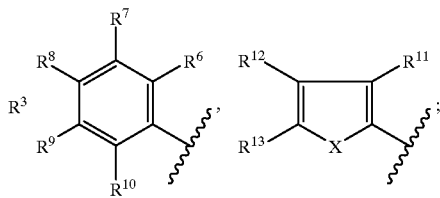

$R^4$ hydrogen, $C_1$–$C_{20}$-alkyl,

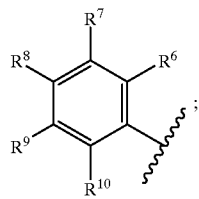

$R^5$ hydrogen, $C_1$–$C_{20}$-alkyl, OH,

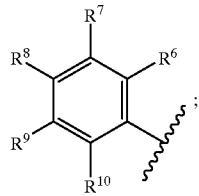

$R^6$ to $R^{13}$ hydrogen, OH, $C_1$–$C_{20}$-alkyl, $C_2$–$C_{10}$-alkenyl, $C_3$–$C_{10}$-cycloalkyl, $C_3$–$C^{10}$-cycloalkenyl, $C_1$–$C_{12}$-alkoxy, $C_1$–$C_{20}$-alkoxycarbonyl, $C_1$–$C_{12}$-alkylamino, $C_1$–$C_{12}$-dialkylamino, aryl, hetaryl, unsubstituted or substituted, substituents which confer solubility in water and are selected from the group consisting of carboxylate, sulfonate or ammonium residues;

X O, S, NH;

n 0, 1.

2. A sunscreen-containing cosmetic or pharmaceutical preparation as defined in claim 1, containing as UV-A filters compounds of the formula I where the variables have the following meanings independently of one another:

$R^1$ and $R^2$ $C_1$–$C_{12}$-alkyl
where $R^1$ and $R^2$ may together form a 5- to 12-membered ring;

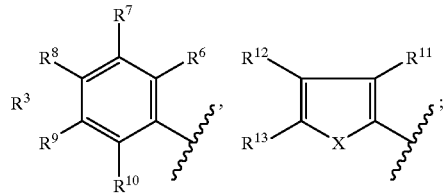

$R^5$ hydrogen;

R6 to $R^{13}$ hydrogen, OH, $C_1$–$C_{12}$-alkyl, $C_1$–$C_8$-alkoxy, $C_1$–$C_{12}$-alkoxycarbonyl, substituents which confer solubility in water and are selected from the group consisting of carboxylate, sulfonate or ammonium residues;

X O, S, NH;

n 0.

* * * * *

UNITED STATES PATENT AND TRADEMARK OFFICE
CERTIFICATE OF CORRECTION

PATENT NO.: 6,132,703

DATED: October 17, 20000

INVENTOR(S): HABECK et al.

It is certified that error appears in the above-identified patent and that said Letters Patent is hereby corrected as shown below:

Col. 19, claim 1, last line in the column, "$C_3$-$C^{10}$-cycloalkenyl" should be --$C_3$-$C_{10}$-cycloalkenyl--.

Col. 20, claim 1, line 6, "X  O" should be --X is O--.

Col. 20, claim 2, line 27, "R6" should be --$R^6$--.

Signed and Sealed this

Eighth Day of May, 2001

Attest:

NICHOLAS P. GODICI

Attesting Officer     Acting Director of the United States Patent and Trademark Office